(12) United States Patent
Banik

(10) Patent No.: US 9,517,298 B2
(45) Date of Patent: Dec. 13, 2016

(54) LOW COST MEDICAL NEEDLE CONTAINER AND MANUFACTURING METHODS THEREFOR

(71) Applicant: Becton, Dickinson and Company, Franklin Lakes, NJ (US)

(72) Inventor: Robert Banik, Edgewater, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 754 days.

(21) Appl. No.: 13/714,044

(22) Filed: Dec. 13, 2012

(65) Prior Publication Data

US 2014/0165505 A1    Jun. 19, 2014

(51) Int. Cl.
*A61M 5/00* (2006.01)
*B65B 43/00* (2006.01)
*B65B 43/08* (2006.01)
*B65B 69/00* (2006.01)

(52) U.S. Cl.
CPC .............. *A61M 5/002* (2013.01); *B65B 43/00* (2013.01); *B65B 43/08* (2013.01); *B65B 69/00* (2013.01)

(58) Field of Classification Search
CPC ..... A61M 5/002; A61M 5/3202; B65B 43/08; B65B 69/00; B65B 43/00
USPC ..... 162/137; 206/524.1, 438, 363–366, 408; 53/477; 604/263; 202/4.21, 4.24
See application file for complete search history.

(56) References Cited

U.S. PATENT DOCUMENTS

| 3,073,307 A * | 1/1963 | Stevens ................. A61M 5/002 |
| | | 206/365 |
| 3,095,972 A * | 7/1963 | Sorenson ............. A61B 19/026 |
| | | 206/365 |
| 3,825,002 A | 7/1974 | Paige |
| 5,545,145 A | 8/1996 | Clinton et al. |
| 5,556,365 A * | 9/1996 | Drummond et al. ......... 493/299 |
| 5,941,857 A | 8/1999 | Nguyen et al. |
| 5,968,021 A | 10/1999 | Ejlersen |
| 6,159,193 A | 12/2000 | Tuerk |
| 6,726,649 B2 | 4/2004 | Swenson et al. |
| 7,645,264 B2 | 1/2010 | Marsh et al. |
| 8,579,115 B2 | 11/2013 | Murphy et al. |
| 2003/0125678 A1* | 7/2003 | Swenson et al. ............. 604/263 |
| 2007/0149924 A1* | 6/2007 | Marsh .......................... 604/117 |
| 2010/0063457 A1 | 3/2010 | Crossman |
| 2012/0022460 A1 | 1/2012 | Horvath et al. |
| 2012/0029440 A1 | 2/2012 | Boyd et al. |
| 2012/0051967 A1* | 3/2012 | Murphy et al. ................. 422/28 |
| 2012/0061274 A1 | 3/2012 | Tumminello et al. |

FOREIGN PATENT DOCUMENTS

EP    0916355    5/1999
EP    1323444 A1    7/2003
(Continued)

*Primary Examiner* — Robert Long
*Assistant Examiner* — Xavier A Madison
(74) *Attorney, Agent, or Firm* — Dickinson Wright PLLC

(57) ABSTRACT

Packaging is disclosed for a medical needle, such as a pen needle, having a hub with a patient end of the needle protruding from a distal end thereof. The packaging includes a tube having a first closed end into which the patient end of the needle is inserted so that the hub contacts an interior of the tube, a second closed end enclosing a proximal end of the hub, and a circumferential region disposed between the proximal end of the hub and the second closed end for opening the package to expose the proximal end of the hub.

17 Claims, 8 Drawing Sheets

(56) References Cited

FOREIGN PATENT DOCUMENTS

| EP | 2201976 | 6/2010 |
|---|---|---|
| GB | 2437923 | 11/2011 |
| WO | WO2010090734 | 8/2010 |

\* cited by examiner

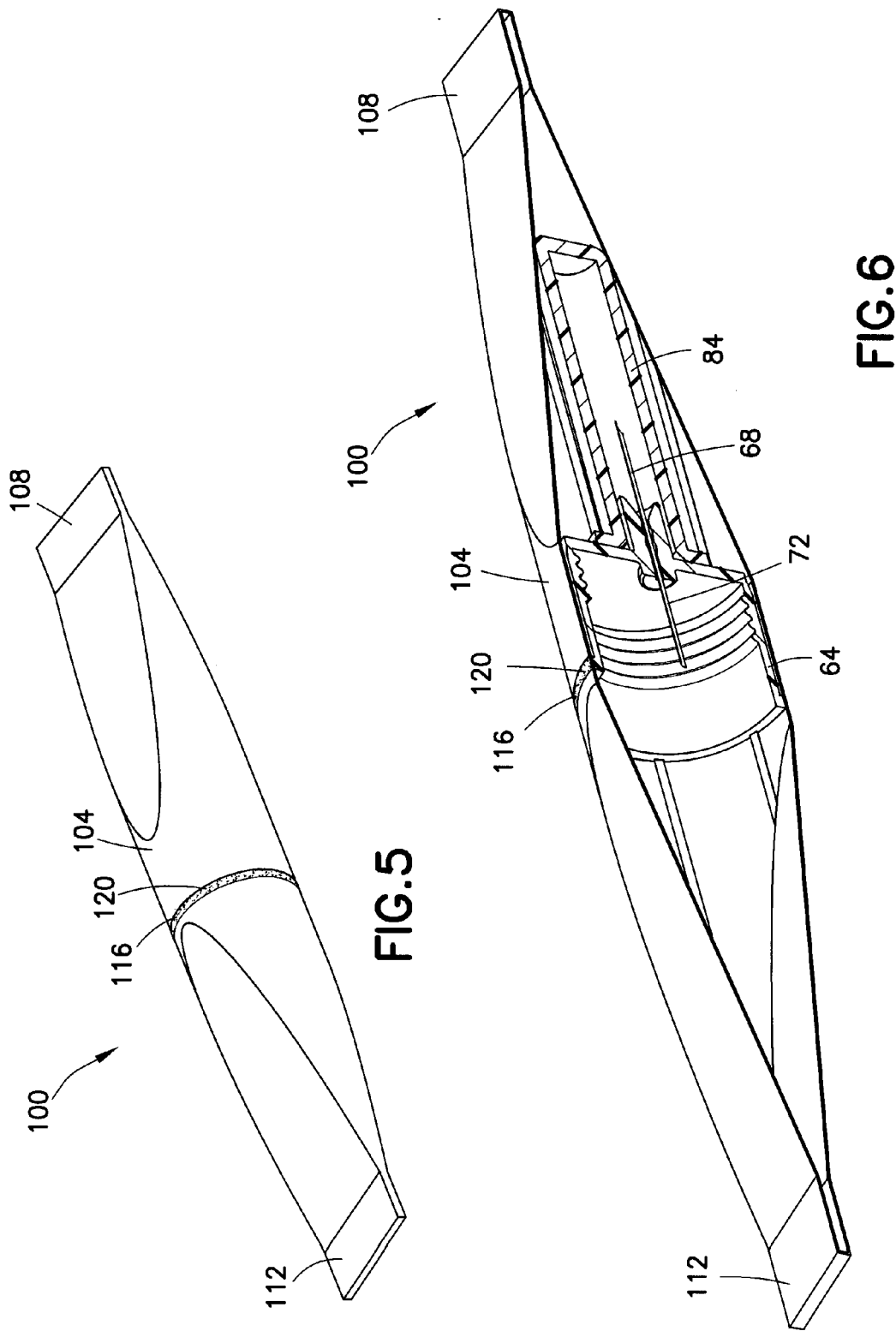

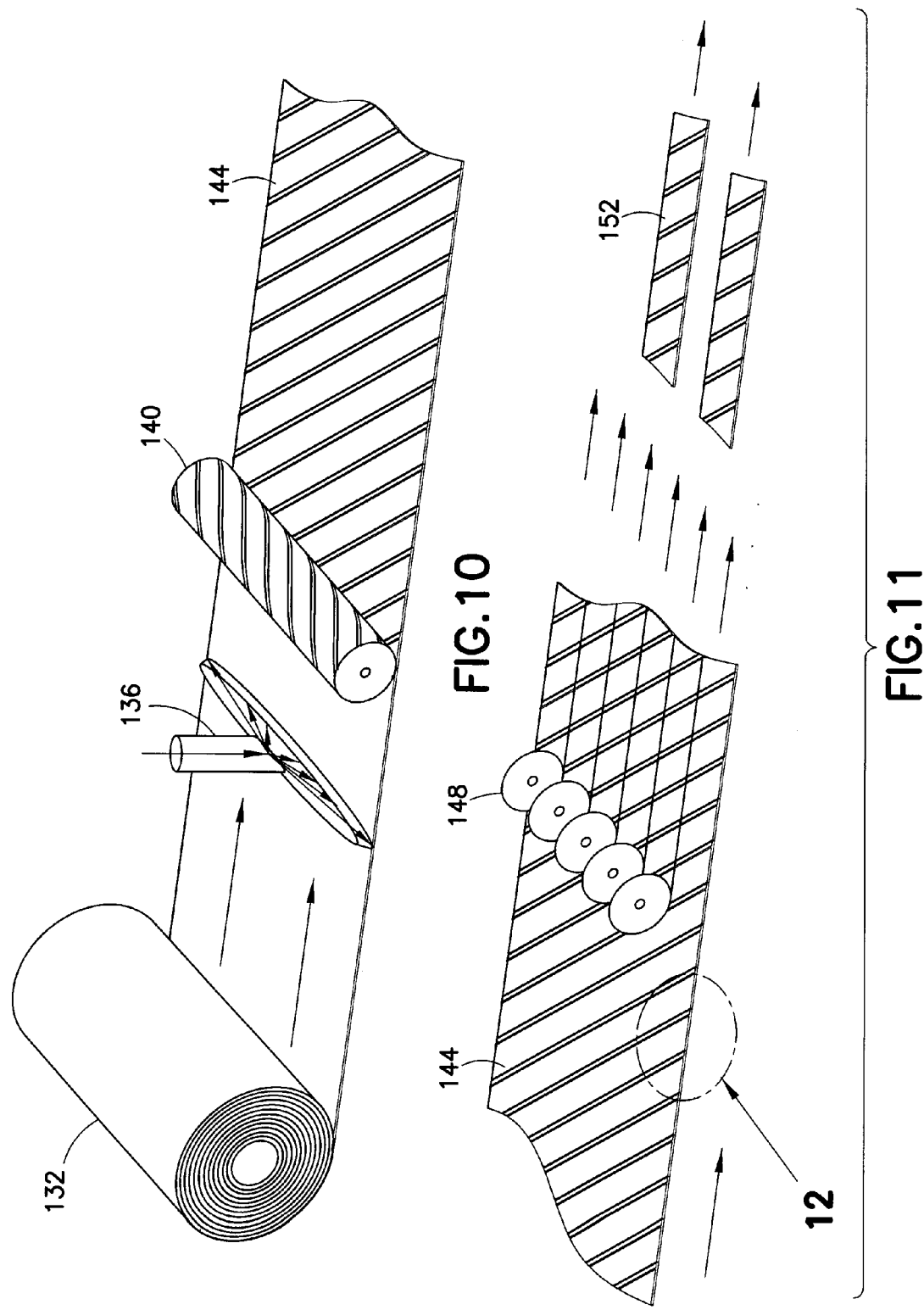

LOW COST MEDICAL NEEDLE CONTAINER AND MANUFACTURING METHODS THEREFOR

BACKGROUND OF THE INVENTION

1. Field of the Invention

The present invention generally relates to needles for a medical injection device, and more particularly, to packaging for dispensing and storing needles for a pen injection device.

2. Description of the Related Art

Medication delivery pens are used for self-injection of precisely measured doses of medication. Pens are widely used, for example, by diabetics to self-inject insulin. A typical medication delivery pen includes a cartridge which contains a volume of liquid medication sufficient for several doses. Using a pen needle attached to the pen device, the dose is injected into a tissue area, such as the intramuscular tissue layer, the subcutaneous tissue layer, or the intradermal tissue layer.

The assembly and operation of a typical pen injection device is described in commonly-assigned U.S. Pat. No. 7,645,264, and a typical pen needle is described in commonly-assigned U.S. Pat. No. 5,941,857, both of which are hereby incorporated by reference in their entirety.

Pen injection devices, such as the exemplary pen injector 50 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen within a lower housing 17. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail herein as they are understood by those knowledgeable of the art.

A pen needle assembly 10 includes a hub 20, a patient needle 11 extending from a patient end of the pen needle assembly, and a septum-penetrating needle cannula 18 disposed within the hub 20 on a non-patient side thereof. The septum-penetrating needle cannula 18 is in fluid communication with the patient needle 11. The hub 20 is preferably screwed onto the lower housing 17, although other attachment means can be used such as attaching directly to the medicament cartridge 12. In attaching the hub 20 to the lower housing 17 or medicament cartridge 12, the septum-penetrating cannula 18 pierces the septum 16, but the septum 16 does not move with respect to the medicament cartridge 12. The stopper 15, however, is axially displaceable within the medicament cartridge 12 while maintaining a fluid-tight seal. The distal movement of the plunger or stopper 15 within the medicament cartridge 12 (due to advancement of the lead screw 7) causes medication to be forced into the patient needle 11 of the hub 20.

To protect a user, or anyone who handles the pen injector 50, a rigid outer shield 29 that attaches to the hub 20, covers the hub 20. The outer shield 29 can also be used as a handle or grip to screw hub 20 onto or off of pen injector 50. Typically, a teardrop-shaped cover or label (not shown), attached to a top flange of the outer shield 29 and having a tab for a handle, provides a sterility barrier for the contents of the outer shield 29. An inner shield or needle cover 28 covers the patient needle 11 within the outer shield 29. The inner shield 28 can be secured to the hub 20 to cover the patient needle 11 by any suitable means, such as an interference fit or a snap fit. The outer shield 29 and inner shield 28 are removed prior to use. The cap 21 fits snugly against outer sleeve 13 to allow a user to securely carry the pen injection device 50.

Pen needle assemblies are usually provided individually packaged inside a plastic cover (such as outer shield 29) with a label covering the opening in the cover to provide a sterility barrier, as described above. These individually packaged pen needle assemblies are often sold packed loosely in a container, such as a box. Boxes of various sizes are used for various quantities of the individually packaged pen needle assemblies (for example, a 50-count box or a 100-count box).

SUMMARY OF EMBODIMENTS OF THE INVENTION

It is an aspect of the present invention to provide packaging for storing and dispensing medical needles, such as pen needles. More specifically, it is an aspect of the present invention to provide packaging for dispensing and storing medical needles prior to their use as well as subsequent to their use. A further aspect of the present invention to provide a method of opening packaging of a medical needle. Additionally, it is an aspect of the present invention to provide a method of packaging medical needles.

The foregoing and/or other aspects of the present invention are achieved by providing packaging for a medical needle having a hub with patient end of the needle protruding from a distal end thereof, the packaging including a tube having a first closed end into which the patient end of the medical needle is inserted so that the hub contacts an interior of the tube, a second closed end enclosing a proximal end of the hub, and a circumferential region disposed between the proximal end of the hub and the second closed end for opening the package to expose the proximal end of the hub.

The foregoing and/or other aspects of the present invention are also achieved by providing a method opening packaging for a medical needle having a hub with patient end of the medical needle protruding from a distal end thereof. The method includes grasping the packaging on opposing axial sides of a substantially circumferential visual indicator, and rotating one of the axial sides relative to the other about an axis substantially perpendicular to a longitudinal axis of the packaging to expose a proximal end of the medical needle hub.

The foregoing and/or other aspects of the present invention are also achieved by providing a method of packaging a medical needle having a hub with patient end of the needle protruding from a distal end thereof. The method includes forming a substantially cylindrical tube, sealing a first end of the tube, inserting the distal end of the needle into the sealed first end of the tube, and sealing a second end of the tube opposite to the first end.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which:

FIG. 5 is a perspective view of a pen needle container in accordance with an embodiment of the present invention;

FIG. 6 is a perspective cross-sectional view of the container of FIG. 5;

FIG. 10 is a perspective view illustrating a process of creating a plastic coating on paper;

FIG. 11 is a perspective view illustrating a process of cutting the paper into strips;

DETAILED DESCRIPTION OF EMBODIMENTS OF THE PRESENT INVENTION

Figure 1:
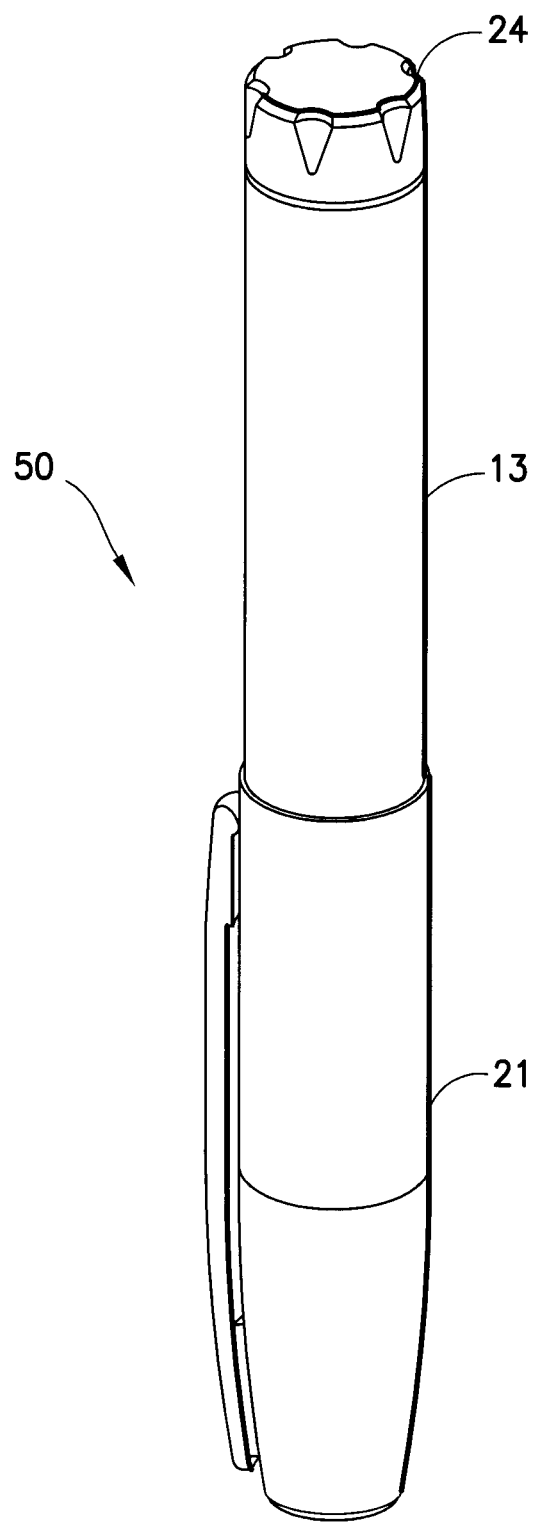
FIG. 1 is a perspective view of an exemplary drug delivery pen.

Reference will now be made in detail to embodiments of the present invention, examples of which are illustrated in the accompanying drawings, wherein like reference numerals refer to the like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

Figure 2:
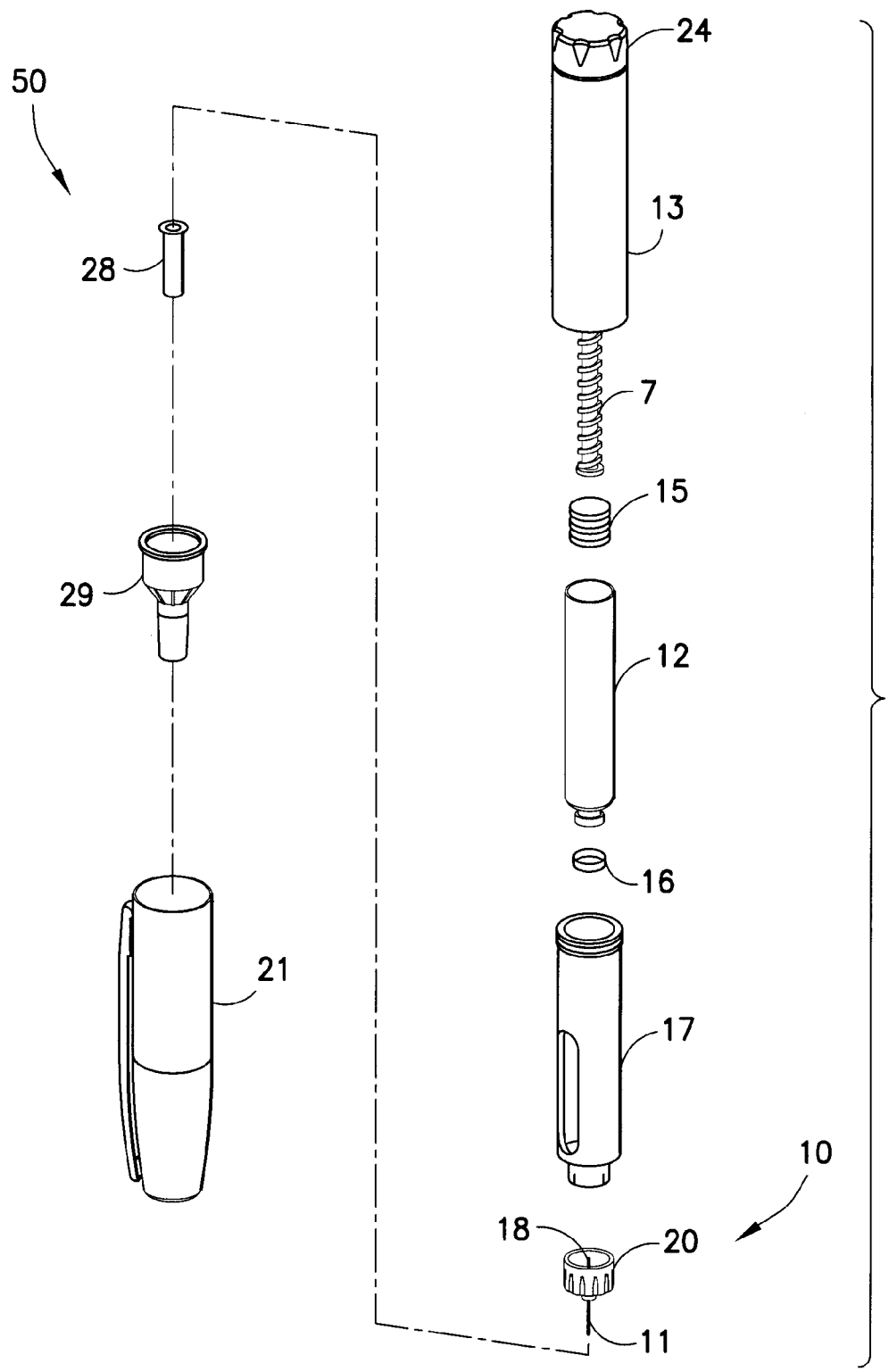
FIG. 2 is an exploded view of the exemplary drug delivery pen of FIG. 1.
Figure 3:
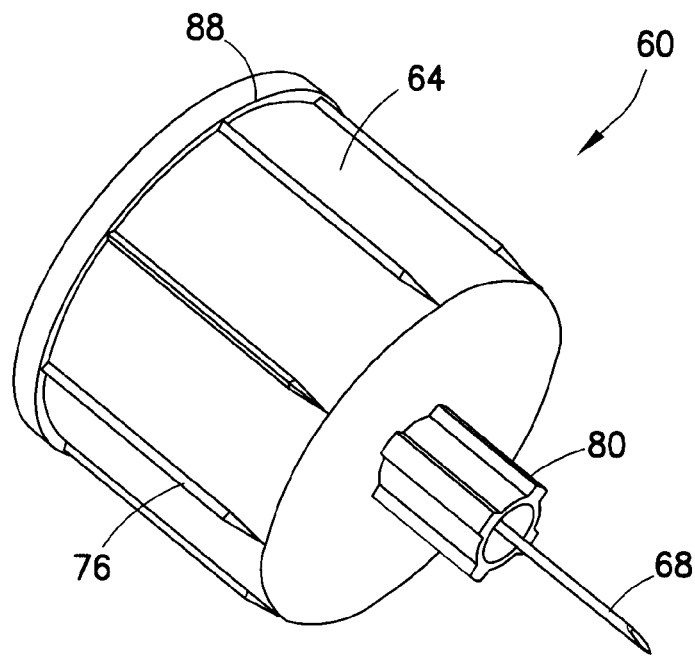
FIGS. 3 and 4 are perspective views of a pen needle assembly that can be used in embodiments of the present invention.
Figure 4:
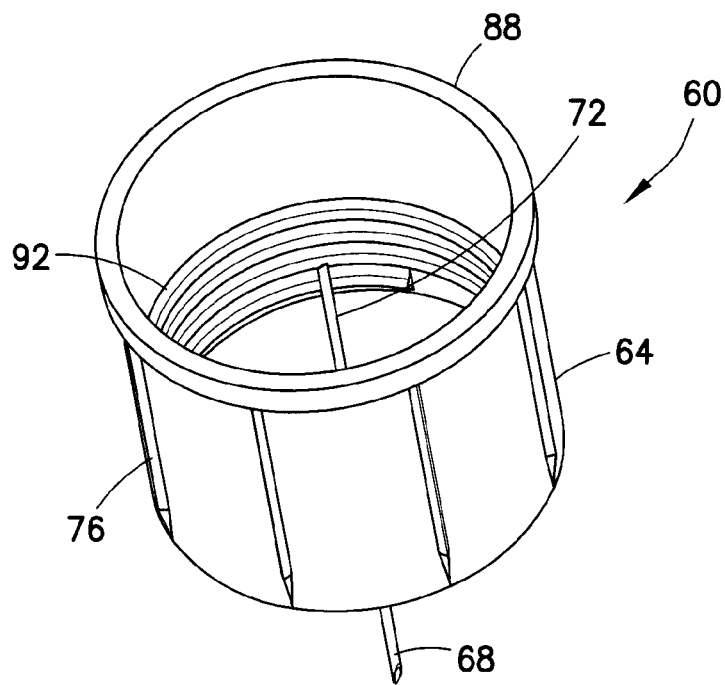

FIGS. 3 and 4 are perspective views of a pen needle assembly 60 that can be used with embodiments of the present invention. For brevity, the phrase "pen needle 60" will be used hereinafter instead of "pen needle assembly 60." Notably, the pen needle 10 of FIG. 2 can also be used with embodiments of the present invention, as can other types of medical needles. Like pen needle 10, pen needle 60 includes a hub 64, a patient needle (or patient end of the needle) 68 extending from a patient end of the pen needle 60, and a septum-penetrating needle cannula 72 disposed within the hub 64 on a non-patient side thereof.

As shown in FIG. 3, the plastic hub 64 is disposed at a non-patient end of the pen needle 60. The hub 64 includes a plurality of ribs or splines 76 for engagement with anti-rotation/retaining structures and/or surfaces that will be described in greater detail below. In addition, protrusion 80 extends from a patient end of the hub 64 and the patient needle 68 extends from the protrusion 80. Optionally, a needle shield 84 (best shown in FIG. 6) can be fitted onto the protrusion 80. The septum-penetrating metal needle cannula 72 (best shown in FIG. 4) disposed within the non-patient end of the hub 64 fluidly communicates with the patient needle 68. The hub 64 also includes a circumferential rim 88 at a proximal end thereof. According to one embodiment, the rim 88 has a larger outer diameter than the splines 76.

Additionally, as shown in FIG. 4, the interior of the non-patient end of the hub 64 includes threads 92 for connection with an injection device, such as the pen injector 50 of FIG. 1. For brevity, hereinafter, the pen injector 50 will be employed as an exemplary injection device. One skilled in the art, however, will appreciate that other types of injection devices may be used without departing from the scope of the present invention. Further, one skilled in the art will appreciate that although pen needles are shown in the exemplary embodiments, embodiments of the present invention can be used with other needles, such as a hypodermic needle with a hub and a patient end of a needle protruding from the hub, without departing from the scope of the present invention.

FIG. 5 is a perspective view of a pen needle packaging or container 100 (hereinafter packaging 100 or container 100 for brevity) in accordance with an embodiment of the present invention, and FIG. 6 is a cross sectional view of the container 100. As shown in FIGS. 5 and 6, the container 100 includes a tube 104 with a first closed end 108 into which the patient end of the needle 68 is inserted so that the hub 64 contacts an interior of the tube 104. Additionally, the container has a second closed end 112 enclosing a proximal end of the hub 64, and a circumferential region 116 disposed between the proximal end of the hub 64 and the second closed end 112 for opening the package 100 to expose the proximal end of the hub 64.

Figure 7:
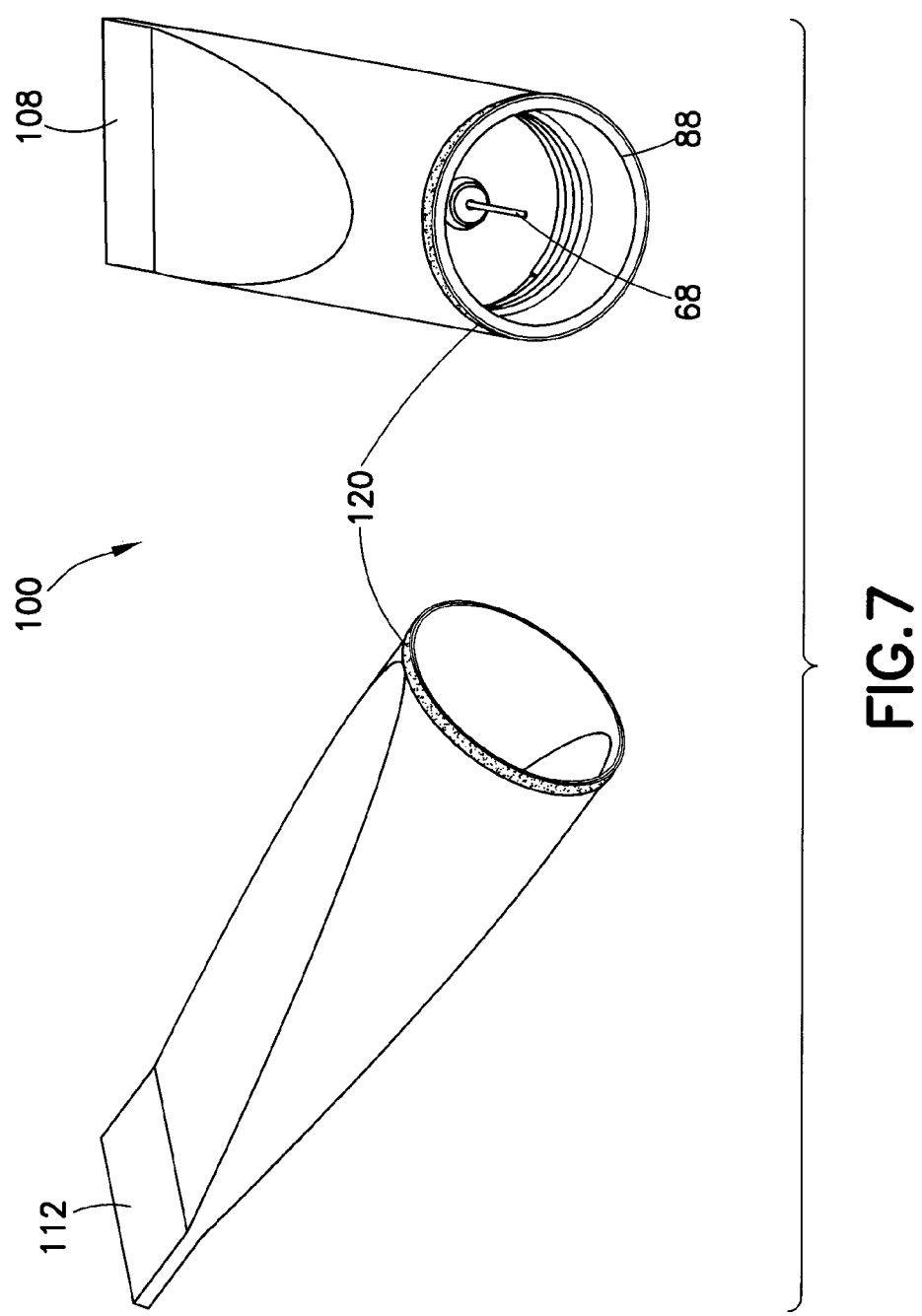
FIG. 7 is a perspective view of the container of FIG. 5 after being opened.

In the circumferential region 116, the stress on the container 100 is not resisted by the hub 64, thus creating a circumferential "tearing" or "popping" line. As shown in FIG. 7, after applying stress to the container 100, for example, by bending the first and second closed ends 108 and 112 in opposite directions, the container 100 opens at the circumferential region, thereby exposing the proximal end of the hub 64. In other words, according to one embodiment, a patient can grasp the container 100 on opposing axial sides of the circumferential region 116, and can expose the proximal end of the needle hub 64 by rotating one of the axial sides relative to the other about an axis substantially perpendicular to a longitudinal axis of the container 100 and "popping" open the container 100 along the circumferential region 116. According to another embodiment, the patient can rotate one of the axial sides relative to the other about an axis that is substantially parallel to the longitudinal axis of the container 100 and "tear" open the container along the circumferential region 116.

According to one embodiment, and as shown in FIGS. 5-7, the circumferential region 116 preferably includes a visual indicator 120 (such as a printed color band) on the exterior of the container 100 denoting the location of the circumferential region 116. If the patient opened the container using one of the above-described methods, the visual indicator 120 would serve as a guide for grasping the container 100 on opposing sides of the circumferential region 116.

According to one embodiment, the circumferential region 116 preferably includes a weakened area to reduce the effort required to circumferentially open the container 100. One manner of creating the weakened area is to score at least a portion of the exterior of the container, for example, at the visual indicator 120 in embodiments that include the visual indicator 120. Another manner of creating the weakened area is to perforate the visual indicator 120. Yet another manner of creating the weakened area is to emboss a portion of the container 100. According to one embodiment described in greater detail below, the weakened area is formed on the interior of the container 100.

According to one embodiment the container 100 includes an insertion depth stop feature for limiting the insertion depth of the needle 60 into the first end 108 of the container 100. In the embodiment shown in FIG. 6, for example, the insertion depth stop feature includes the first closed end 108 that interferes with the needle sleeve 84 covering the patient end 68 of the needle. The insertion depth stop feature positions the inserted pen needle 60 within the container 100 to aid positioning of the circumferential region 116, the visual indicator 120, and/or the weakened area.

Figure 8:
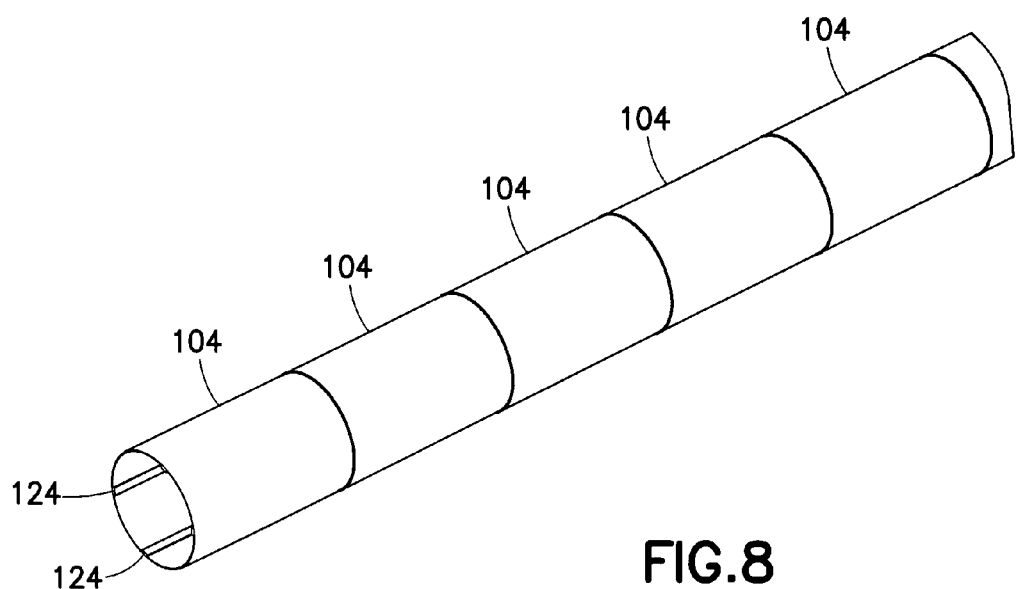
FIG. 8 is a perspective view of an extruded tube for manufacturing the container of FIG. 5.
Figure 9:
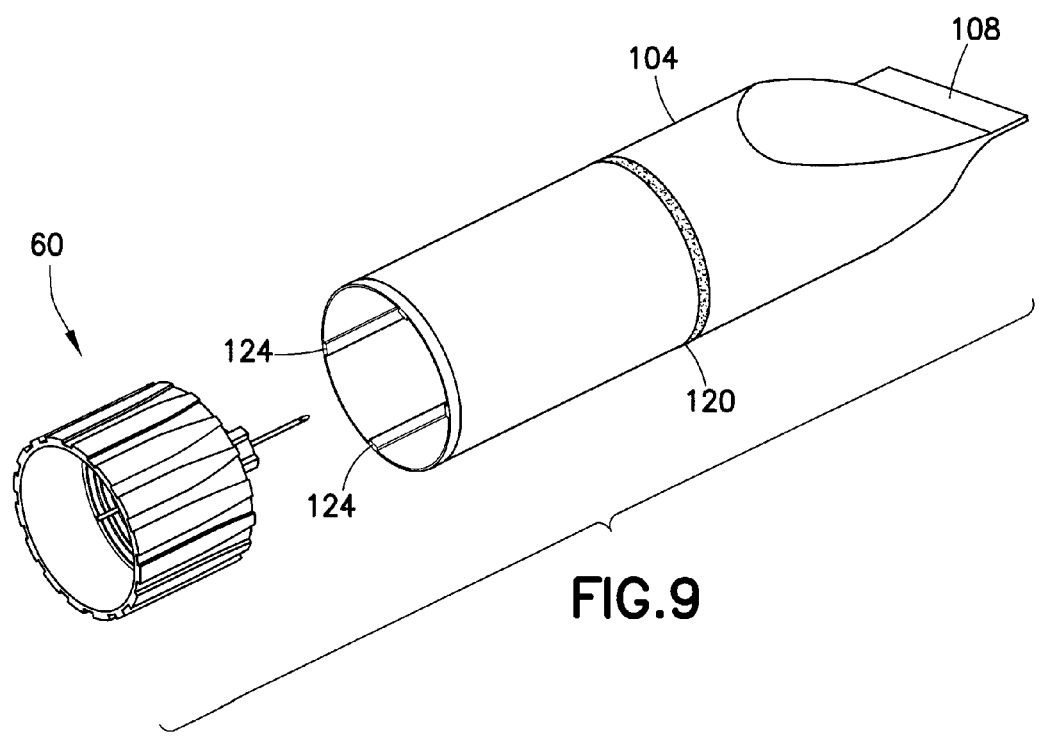
FIG. 9 is a perspective view illustrating insertion of the pen needle assembly of FIG. 3 into an unfinished container of FIG. 5.

According to one embodiment, the tube 104 can be formed by extrusion. FIG. 8 illustrates a plurality of tubes 104 extruded as a single tube. The individual tubes 104 can be subsequently cut to unit length using conventional methods. After the first end 108 of the individual tube 104 is closed, as shown in FIG. 9, the distal end of pen needle 60 is inserted into the tube 104. The ends 108 and 112 can be closed, for example, by using an adhesive or by pinching and heat-sealing. Subsequent to the pen needle insertion, the second the second end 112 of the tube 104 is closed.

According to one embodiment, the tube 104 is extruded plastic, such as polyethylene (PE) or polypropylene (PP). According to another embodiment, the tube 104 is plastic coextruded over paper, paperboard, or cardboard. For example, the plastic may be on the interior of the tube and the paper may be on the exterior of the tube 104. The use of plastic, such as PE or PP, lends itself to crimping or pinching and heat-sealing the ends 108 and 112 of the container 100. According to one embodiment, the manufacturer forms plastic only on the interior of the paper tube 104. According to another embodiment, the manufacturer forms plastic on both the interior and the exterior of the paper tube 104. According to yet another embodiment, the manufacturer forms plastic on the inside of the paper tube 104 and forms a water-resistant wax coating on the exterior of the tube 104. In contrast to having paper on the exterior of the tube 104, such exterior coatings (wax and/or plastic) are very clean, i.e., the wax and/or plastic does not shed or generate particulate matter.

According to one embodiment, the tube 104 can be slightly undersized relative to the hub 64, so that after inserting the pen needle 60, the fit between the tube 104 and the pen needle 60 is sufficiently tight to transmit torque, and thereby facilitate attachment of the pen needle 60 to the pen injector 50 while the pen needle 60 is retained in the first end 108 of the container 100. According to another embodiment, the splines 76 of the hub 64 can engage the interior surface of the tube 104 to resist rotation and facilitate attachment of the pen needle 60 to the pen injector 50. According to yet another embodiment the tube 104 can be sufficiently flexible that a user can grasp the container 100 to prevent rotation of the pen needle 60 during attachment of the pen injector 50.

By extruding the tube 104, an anti-rotation feature can be formed on an interior of the tube 104 during the extrusion. For example, as shown in FIGS. 8 and 9, the tube 104 includes a plurality of axial splines 124. The axial splines 124 engage the hub 64 and prevent rotation of the pen needle 60, thereby facilitating attachment of the pen needle 60 to the pen injector 50 while the pen needle 60 is retained in the first end 108 of the container 100. After injection of a medicament, the patient can re-insert the pen needle 60 into the first end 108 and use the anti-rotation of the splines 124 to remove the pen needle 60 from the pen injector 50. Subsequently, the patient can safely dispose of the pen needle 60.

According to one embodiment, the tube 104 includes spiral-wrapped paper, paperboard, or cardboard. Spiral-wrapped paper has been used for packaging paper towels, wrapping paper, and food, such as biscuits. Typically, to make plastic-coated spiral-wrapped paper, a wide roll of raw paper is unrolled and then coated with the plastic. The coated paper then passes under a smooth pressure roller to control the thickness of the layer of plastic. Subsequently, the paper is cut into long strips that are fed into paper tube forming machines, where an adhesive is applied and the strips are formed into tubes with a spiral seam.

By adding texture to the pressure roller, however, a textured pattern or patterns can be formed in the plastic coating. For example, as shown in FIGS. 10-13, by employing a texture on the pressure roller that has an angle relative to the rotational axis of the pressure roller, and accounting for the angle of the spiral seam, a textured pattern can be formed in the plastic layer that results in a circumferential feature or features in the finished spiral tube.

More specifically, in FIG. 10, as a roll of paper 132 unwinds, an extrusion coater 136 coats the paper 132 with a layer of plastic, such as PE or PP. A textured pressure roller 140 then controls the thickness of the layer of plastic and imprints a directional pattern in the plastic layer to form textured paper 144. Optionally, the paper 132 can have a coating on the other side as well. Preferably, such an additional coating, such as plastic or wax, is applied prior to or at the same time as the application of the textured pressure roller 140. As shown in FIG. 11, slitters 148 cut the textured paper 144 into textured strips 152, which are subsequently fed into conventional paper tube forming machines. After forming the long spiral tubes, the spiral tubes are cut to a unit length to form the tube 104. As previously described, the first end 108 is subsequently sealed, the pen needle 60 is inserted into the first end 108, and the second end 112 is sealed to form the container 100.

Figure 12:
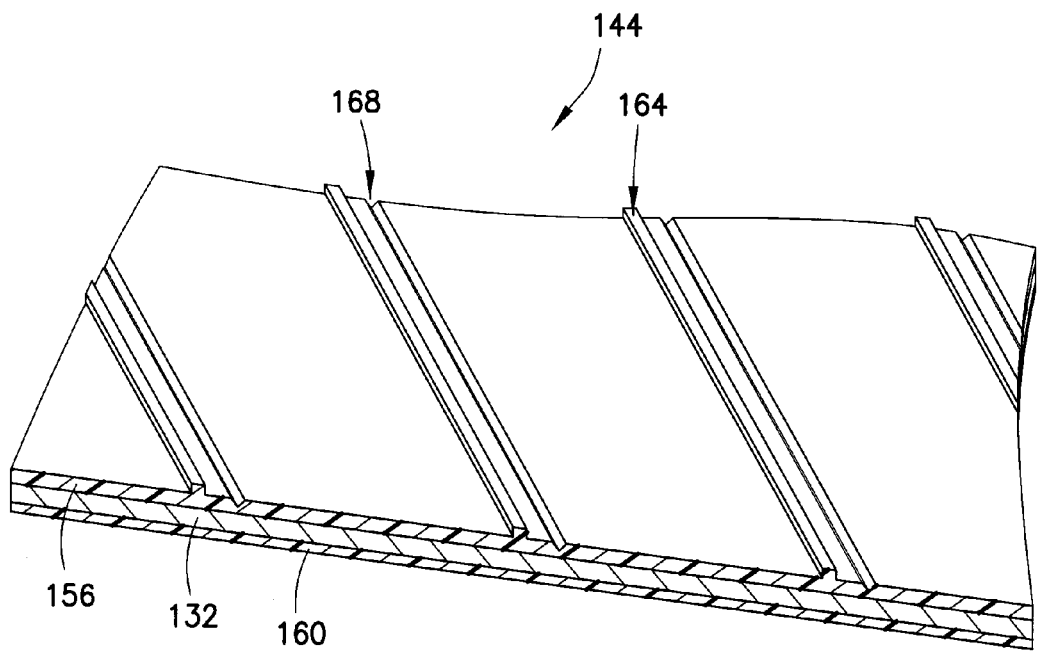
FIG. 12 is a perspective cutaway view of the paper of FIG. 11.

FIG. 12 is a perspective cutaway view of the textured paper 144. The textured paper 144 includes the paper layer 132 and the plastic layer 156 applied by the extrusion coater 136. Preferably, the textured paper 144 also includes an additional coating 160, such as plastic or wax, on the other side of the paper 132. According to one embodiment, because of the textured roller 140, the plastic layer 156 includes a raised feature 164 and a recessed feature 168 that are formed at an angle to the direction of travel of the textured paper 144.

Figure 13:
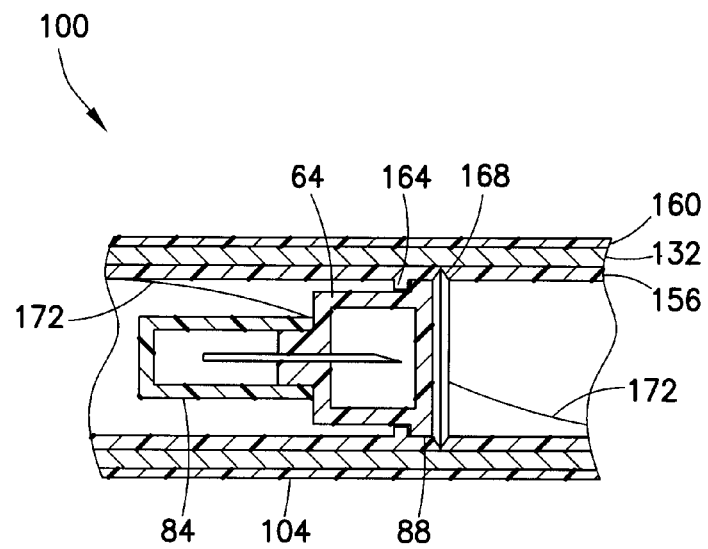
FIG. 13 is a partial cross-sectional view of a container in accordance with an embodiment of the present invention.

As shown in FIG. 13, once a spiral seam 172 is formed by the spiral wrapping and the tube 104 is cut to unit size, the raised feature 164 has become a circumferential depth stop or stop ledge 164 on the interior of the tube 104 for engaging the rim 88 of the inserted pen needle 60. In addition to functioning as the insertion depth stop, the raised feature 164 can also serve as an anti-rotation feature by engaging the splines or crush ribs 76 of the hub 64. In such an embodiment, the rim or outer flange 88 has a greater outer diameter than the splines 76. One skilled in the art will appreciate that the axial thickness of the circumferential depth stop 164 can be adjusted to provide the desired anti-rotation performance while maintaining the desired ease of patient withdrawal of the pen needle 60 from the container 100. According to another embodiment, not shown, by altering the textured pattern on the textured pressure roller 140, the interior of the tube 104 can include the insertion depth stop 164 and anti-rotation axial splines, such as the axial splines 124 shown in FIGS. 8 and 9.

In addition, as shown in FIG. 13, the recessed feature 168 has become a circumferential weakened area on the interior of the tube 104 to ease the circumferential opening of the container 100. One skilled in the art will appreciate that although the depth stop and the weakened area are shown as being circumferential, such features may be circumferentially discontinuous without departing from the scope of the present invention.

Although only a few embodiments of the present invention have been shown and described, the present invention is not limited to the described embodiments. Instead, it will be appreciated by those skilled in the art that changes may be made to these embodiments without departing from the principles and spirit of the invention as defined in the appended claims and their equivalents.

What is claimed is:

1. Packaging for a medical needle having a hub with a patient end of the medical needle protruding from a distal end thereof, the packaging comprising:
    a tube having:
        a first closed end;
        a second closed end; and
        a circumferential region disposed between the first and second closed ends for opening the package to allow removal of the medical needle; and
    axial splines on an interior of the tube for engaging the needle hub to prevent rotation of the medical needle relative to the packaging;
    wherein the tube is formed of a single piece of material; and
    the single piece of material breaks at the circumferential region to allow removal of the medical needle.

2. The packaging according to claim 1, further comprising a visual indicator on an exterior of the circumferential region indicating its location.

3. The packaging according to claim 1, wherein the circumferential region comprises a weakened area to ease breaking the single piece of material at the circumferential region.

4. The packaging according to claim 3, wherein the weakened area comprises external scoring.

5. The packaging according to claim 3, wherein the weakened area comprises a perforation.

6. The packaging according to claim 1, further comprising an insertion depth stop feature for limiting an insertion depth of the medical needle into the packaging.

7. Packaging for a medical needle having a hub with a patient end of the medical needle protruding from a distal end thereof, the packaging comprising:
    a tube having:
        a first closed end;
        a second closed end; and
        a circumferential region disposed between the first and second closed ends for opening the package to allow removal of the medical needle;
    wherein the tube is formed of a single piece of material;
    the single piece of material breaks at the circumferential region to allow removal of the medical needle; and
    the weakened area is disposed only on an interior of the tube.

8. Packaging for a medical needle having a hub with a patient end of the medical needle protruding from a distal end thereof, the packaging comprising:
    a tube having:
        a first closed end;
        a second closed end; and
        a circumferential region disposed between the first and second closed ends for opening the package to allow removal of the medical needle; and
    an insertion depth stop feature for limiting an insertion depth of the medical needle into the packaging;
    wherein the tube is formed of a single piece of material;
    the single piece of material breaks at the circumferential region to allow removal of the medical needle; and
    the insertion depth stop feature comprises one of:
        the first closed end that interferes with an inner shield covering the patient end of the medical needle; or
        an at least partial circumferential protrusion disposed on an interior of the tube for engaging an outer flange on the hub of the medical needle.

9. The packaging according to claim 8, wherein the circumferential protrusion additionally engages splines on the hub to prevent rotation of the medical needle relative to the packaging.

10. Packaging for a medical needle having a hub with a patient end of the medical needle protruding from a distal end thereof, the packaging comprising:
    a tube having:
        a first closed end;
        a second closed end; and
        a circumferential region disposed between the first and second closed ends for opening the package to allow removal of the medical needle
    wherein the tube is formed of a single piece of material;
    the single piece of material breaks at the circumferential region to allow removal of the medical needle; and
    the material comprises spiral-wrapped paper.

11. The packaging according to claim 10, wherein the material comprises a plastic coating on an interior thereof.

12. The packaging according to claim 10, wherein the material comprises a coating on an exterior thereof, the exterior coating comprising one of plastic or wax.

13. A method of packaging a medical needle having a hub with a patient end of the needle protruding from a distal end thereof, the method comprising:
    forming a substantially cylindrical tube;
    sealing a first end of the tube;
    inserting the entire medical needle through a second end of the tube opposite to the first end; and
    subsequent to the inserting, sealing the second end of the tube;
    wherein forming the tube comprises:
        coating a first side of a paper with a plastic layer;
        adding texture to the plastic layer with a pressure roller; and
        spirally adhering the paper to itself with the plastic layer on an interior of the tube.

14. A method of packaging a medical needle having a hub with a patient end of the medical needle protruding from a distal end thereof, the method comprising:
    forming a substantially cylindrical tube;
    sealing a first end of the tube;
    inserting the distal end of the medical needle into the sealed first end of the tube; and
    sealing a second end of the tube opposite to the first end;
    wherein forming the tube comprises co-extruding paper and plastic layers of the tube.

15. The method according to claim 13, further comprising coating a second side of the paper with one of a wax or plastic.

16. The method according to claim 13, wherein adding the texture comprises forming one of a raised feature and a recessed feature in the plastic layer at an angle to a rotational axis of the pressure roller.

17. The method according to claim 16, wherein adding the texture further comprises forming the remaining one of the raised feature and the recessed feature in the plastic layer at the angle to the rotational axis of the pressure roller.

\* \* \* \* \*